(12) United States Patent
Park et al.

(10) Patent No.: US 7,300,454 B2
(45) Date of Patent: Nov. 27, 2007

(54) CATHETER APPARATUS FOR PERCUTANEOUS CORONARY INTERVENTION CAPABLE OF ACCURATELY POSITIONING STENT AND BALLOON IN A DESIRED POSITION

(75) Inventors: Jeong Euy Park, Seoul (KR); Hyuk Nam Kwon, Seoul (KR)

(73) Assignee: Samsung Life Public Welfare Foundation, Seoul (KR)

( * ) Notice: Subject to any disclaimer, the term of this patent is extended or adjusted under 35 U.S.C. 154(b) by 469 days.

(21) Appl. No.: 10/527,123

(22) PCT Filed: Jul. 4, 2003

(86) PCT No.: PCT/KR03/01321

§ 371 (c)(1),
(2), (4) Date: Mar. 8, 2005

(87) PCT Pub. No.: WO2004/021930

PCT Pub. Date: Mar. 18, 2004

(65) Prior Publication Data

US 2005/0240210 A1    Oct. 27, 2005

(30) Foreign Application Priority Data

Sep. 9, 2002    (KR) .................. 10-2002-0054323

(51) Int. Cl.
*A61F 2/06*    (2006.01)
(52) U.S. Cl. .................................. 623/1.11
(58) Field of Classification Search .............. 623/1.11; 606/108, 200; 604/159, 528
See application file for complete search history.

(56) References Cited

U.S. PATENT DOCUMENTS

| | | | | |
|---|---|---|---|---|
| 4,921,484 A | * | 5/1990 | Hillstead | 604/104 |
| 5,433,723 A | * | 7/1995 | Lindenberg et al. | 606/198 |
| 6,077,273 A | | 6/2000 | Euteneuer et al. | |
| 6,146,415 A | * | 11/2000 | Fitz | 623/1.11 |
| 6,623,474 B1 | * | 9/2003 | Ponzi | 604/528 |

(Continued)

FOREIGN PATENT DOCUMENTS

EP    819 413 B    12/2004

(Continued)

*Primary Examiner*—Matthew S. Gart
*Assistant Examiner*—Eric Blatt
(74) *Attorney, Agent, or Firm*—Frommer Lawrence & Haug LLP; Ronald R. Santucci (57) ABSTRACT

A catheter apparatus for percutaneous coronary intervention (PCI) capable of accurately positioning the balloon and stent in a desired position includes an introducer set fixed to an opening of the human artery, a guiding catheter secured to the introducer set and introduced into the artery, a Y-connector coupled with the guiding catheter, a guidewire introduced into the guiding catheter, a balloon catheter introduced into the guiding catheter and having a balloon at the distal end thereof, a minute adjustment portion having a nut and a bolt for minutely adjusting the insertion portion of the balloon catheter in the artery, a combining frame having two legs eachcoupled with the main tube and the nut, respectively, and a clamping portion for holding the balloon catheter firmly in position. The catheter apparatus provided by the present invention helps the physician to place the balloon and stent more accurately in the desired position of the artery so that the PCI operation becomes more accurate, easier and safer.

11 Claims, 13 Drawing Sheets

U.S. PATENT DOCUMENTS

| | | | |
|---|---|---|---|
| 6,669,714 B2 * | 12/2003 | Coleman et al. | 606/219 |
| 7,011,682 B2 * | 3/2006 | Lashinski et al. | 623/2.37 |
| 2003/0040735 A1 * | 2/2003 | Kunis et al. | 604/528 |
| 2004/0193180 A1 * | 9/2004 | Buzzard et al. | 606/108 |
| 2005/0027305 A1 * | 2/2005 | Shiu et al. | 606/108 |

FOREIGN PATENT DOCUMENTS

| | | |
|---|---|---|
| JP | 09-173465 | 7/1997 |
| KR | 1999-0067500 | 8/1999 |
| WO | WO 97/17898 | 5/1997 |

* cited by examiner

CATHETER APPARATUS FOR PERCUTANEOUS CORONARY INTERVENTION CAPABLE OF ACCURATELY POSITIONING STENT AND BALLOON IN A DESIRED POSITION

This application is a 371 ofPCT/KR2003/001321 filed on Jul. 4, 2003, published on Mar. 18, 2004 under publication number WO 2004/021930 A1 which claims priority benefits from Korean patent application number KR 10-2002-0054323 filed Sep. 9, 2002.

BACKGROUND OF THE INVENTION

1. Field of the Invention

The present invention relates to an improved catheter apparatus for percutaneous coronary intervention (PCI), and more particularly to a catheter apparatus for PCI whereby a balloon catheter can be moved more accurately to place a balloon formed at the distal end of the balloon catheter and a stent mounted on the balloon in a position of a human coronary artery having a cardiovascular disease such as a stenotic lesion.

2. Description of the Related Art

Coronary arteries of a human blood circulation system are tubes that supply the heart with oxygen, blood and nutritive substances. The left and right coronary arteries branching off from the ascending aorta spread over the surface of the heart as if to enclose the heart.

PCI has recently become a commonly performed technique for treating cardiovascular diseases such as stenotic lesions and abrupt vessel closure of coronary arteries. A stenotic lesion is an abnormal narrowing of an artery usually due to atherosclerosis.

More than 15,000 PCI procedures are performed yearly in the Republic of Korea, and it has been estimated that more than 100,000 procedures are performed annually in Japan and more than 1,000,000 procedures are performed annually in the U.S.

In PCI treatment, a balloon catheter is inserted through a femoral or brachial artery of the patient to introduce the balloon formed at the distal end of the balloon catheter to the obstructive lesion of the coronary artery. Next, inflation of the balloon with a fluid (i.e. contrast media) causes the obstructive lesion of the coronary artery to become more open.

PCI treatment also involves the introduction into the coronary artery of a stent, which generally has a metal tubular meshwork structure and is mounted on the inflatable balloon at the distal end of the balloon catheter, through the femoral artery or the brachial artery, and the introduction of the balloon and the stent to the stenotic lesion of the coronary artery. Subsequently, the balloon is inflated with a fluid which expands the stent causing the stent to undergo a plastic deformation, thereby installing the stent within the walls of the coronary artery. After the balloon is deflated and pulled back out of the lesion, the stent is left behind in place so as to keep the blockage open by continuously supporting the interior walls of the artery with radial force.

Figure 1A:
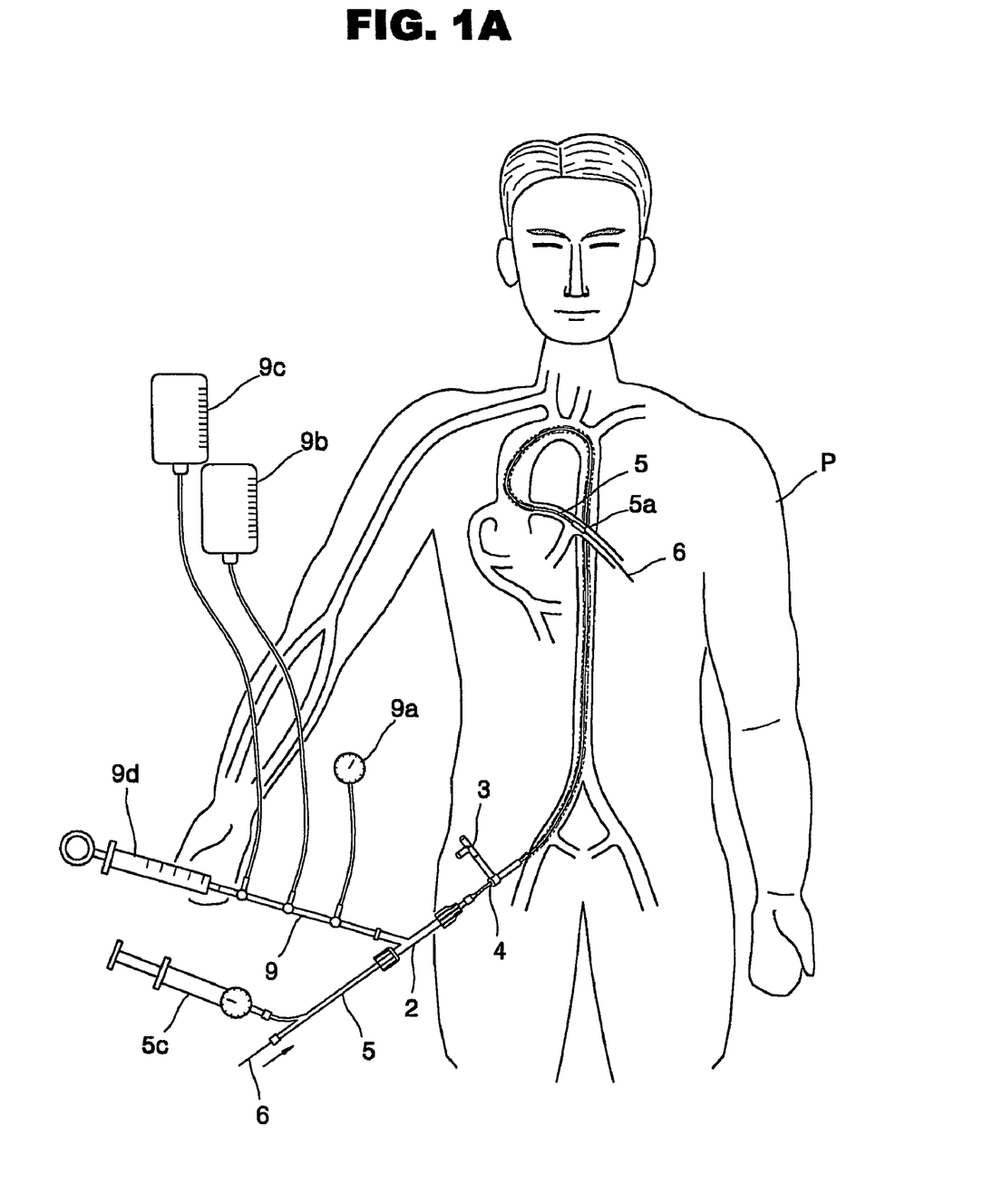
FIG. 1A is an illustration of the PCI treatment using the conventional catheter apparatus including a guidewire, a balloon catheter, etc.
Figure 1B:
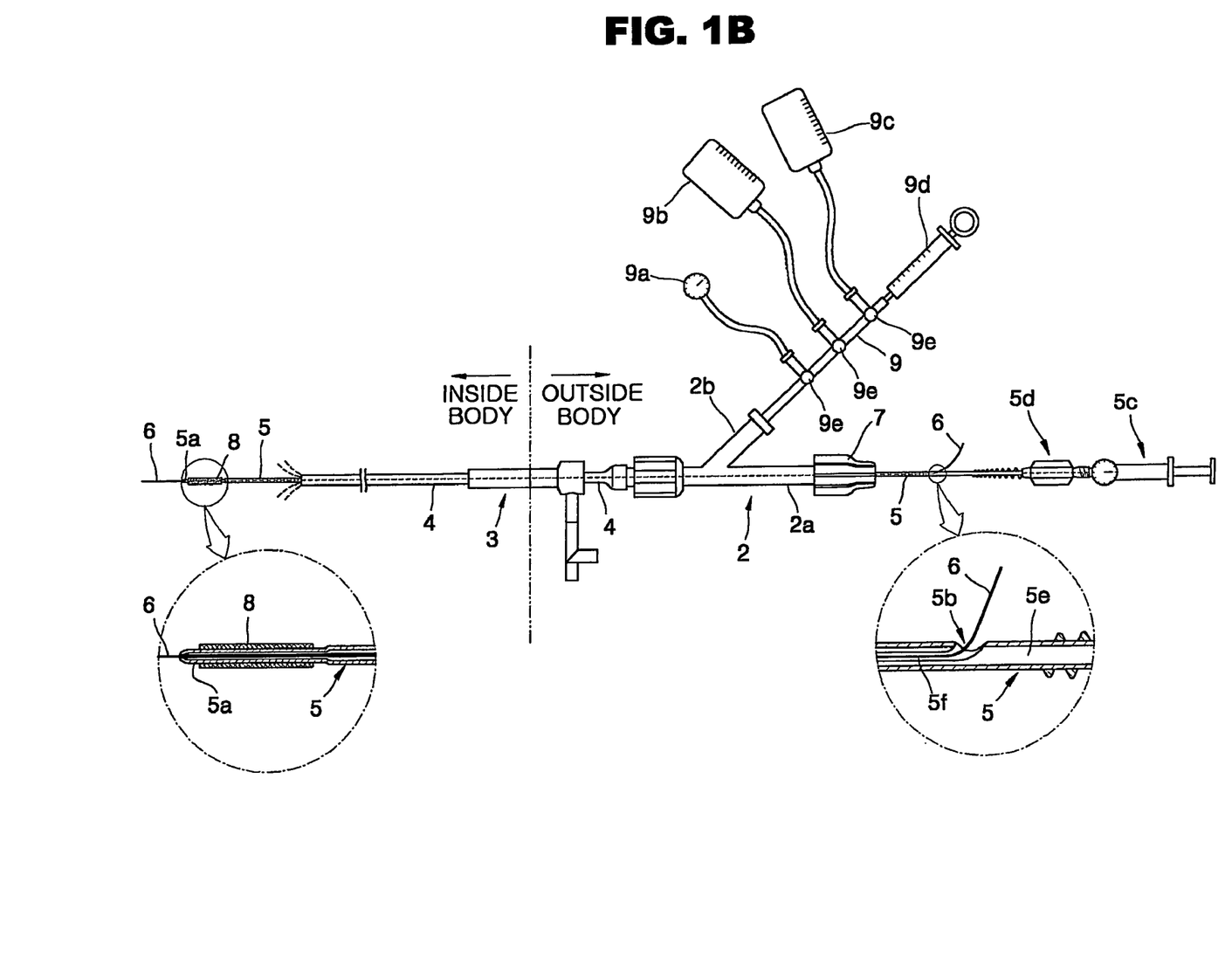
FIGS. 1B and 1C are illustrations of the conventional catheter apparatus for PCI including the balloon catheter shown in FIG. 1A.
Figure 1C:
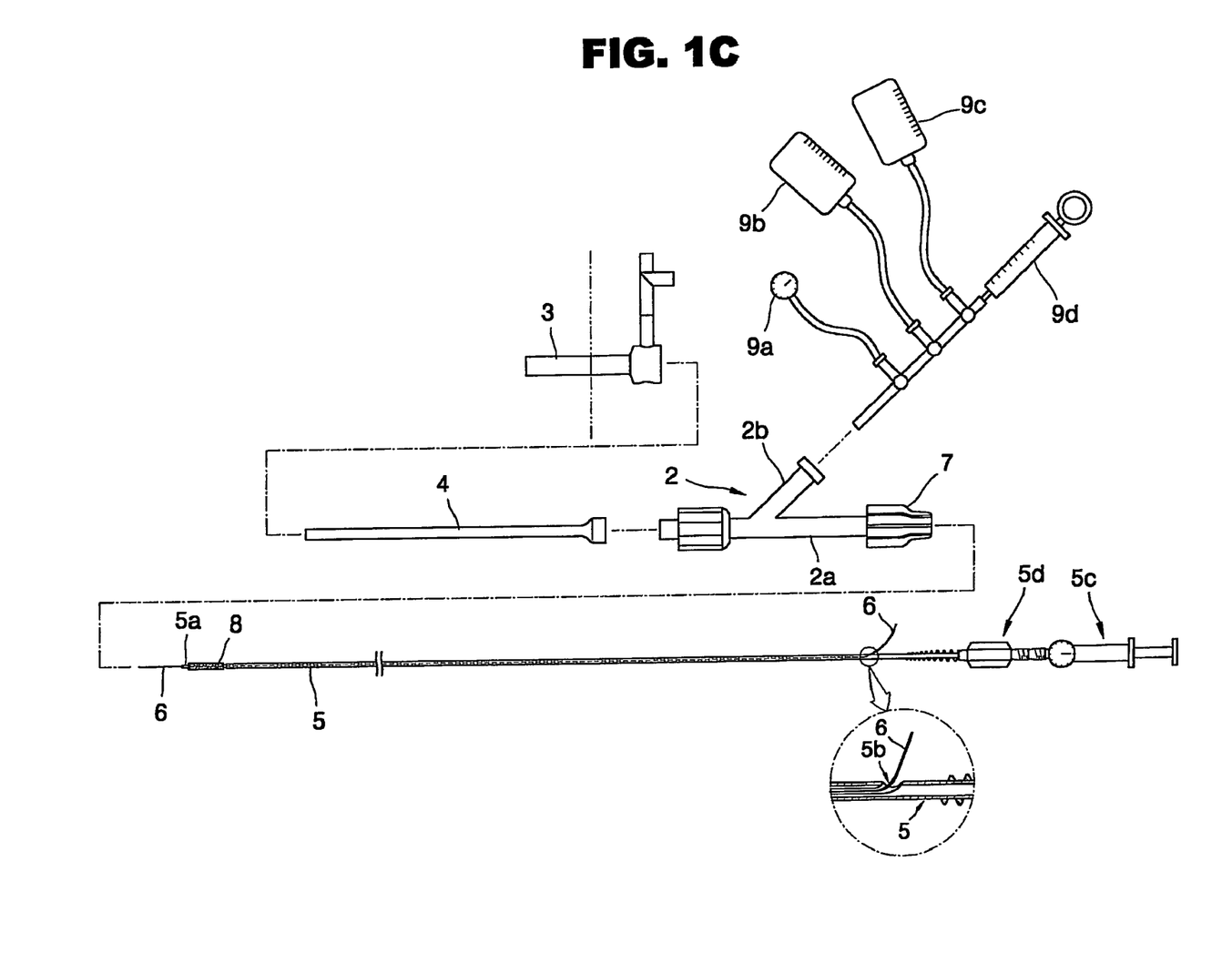
Figure 1D:
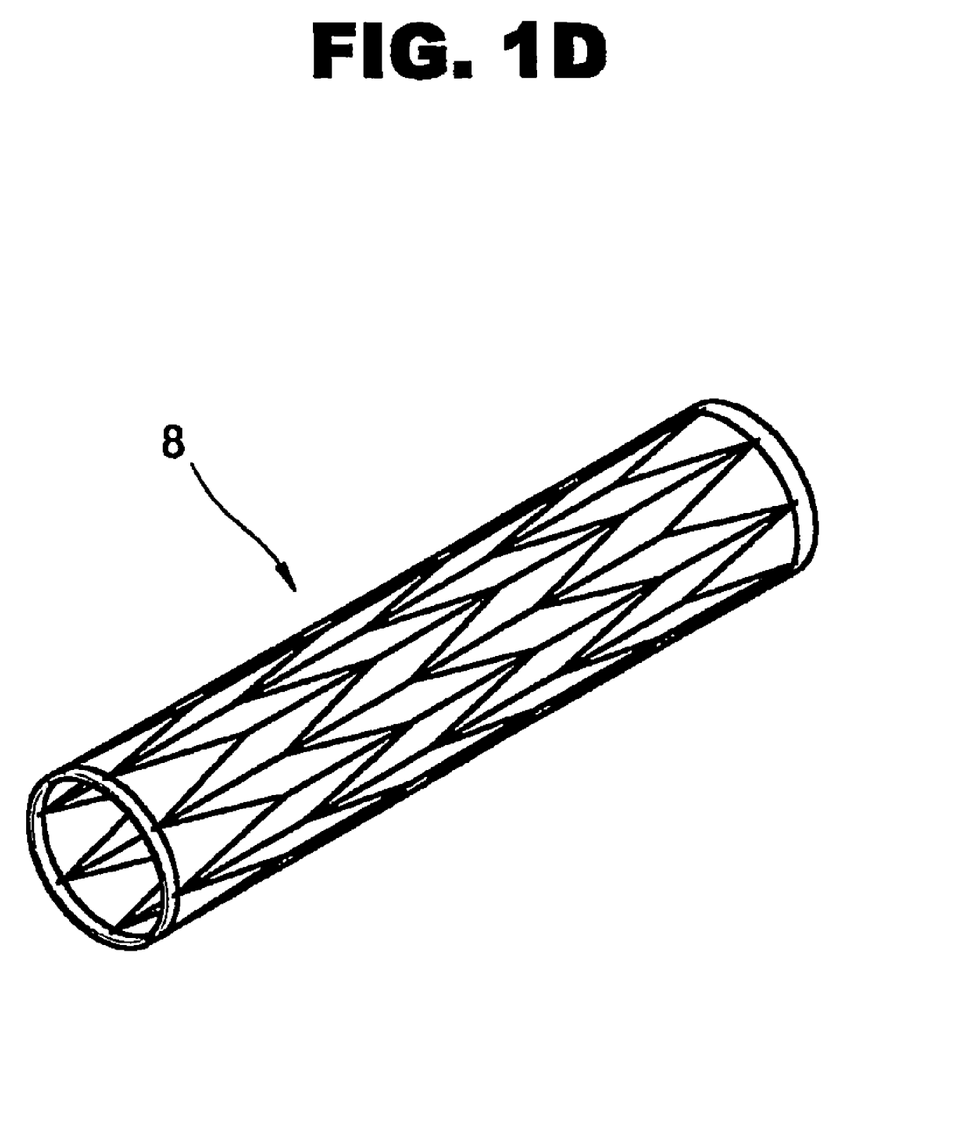
FIG. 1D shows the stent mounted on the balloon formed at the distal end of the balloon catheter, the stent being inserted into the coronary artery by means of the balloon catheter.

FIG. 1B is an illustration of the conventional catheter apparatus 1 for PCI including a balloon catheter, a guiding catheter, etc., in which all parts of the apparatus are assembled. FIG. 1C is an illustration of the catheter apparatus 1 shown in FIG. 1B, in which certain pieces are disassembled from the whole apparatus. FIG. 1D is an illustration of a stent 8 mounted on the inflatable balloon 5a at the distal end of the balloon catheter 5 shown in FIGS. 1B and 1C.

A conventional catheter apparatus 1 for PCI includes a Y-connector 2, an introducer set 3, a guiding catheter 4, a balloon catheter 5, a guidewire 6, a clamp 7 and a stent 8. Among these components, the Y-connector has a main tube 2a and a side tube 2b. The guiding catheter 4 which is introduced into the introducer set 3 is coupled with the main tube 2a of the Y-connector 2. The guidewire 6 and the balloon catheter 5 pass through the main tube 2a of the Y-connector 2, and the side tube 2b is coupled with a pipe of a manifold 9.

The manifold 9 has a plurality of pipes that are coupled with a pressure sensing device 9a, a physiological saline solution bottle 9c and a contrast media injection syringe 9d, respectively. In addition, the manifold 9 has a plurality of valves for controlling the flows of several fluids, installed inside the pipes of the manifold 9, respectively.

As much as is needed of the contrast media contained in the contrast media bottle 9c may be injected into the patent's artery by way of the contrast media injection syringe 9d.

The balloon catheter 5 has a dual lumen structure in which a guidewire passage lumen 5f extends through a contrast media passage lumen 5e. A balloon 5a is integrally formed at the distal end of the balloon catheter 5 which is introduced into the artery. The balloon catheter 5 has a balloon inflation port 5d at its proximal end. The guidewire passage lumen 5f extends from the distal end of the balloon catheter 5 to a guidewire passage opening 5b at a predetermined position of the balloon catheter 5 where the guidewire exits from the balloon catheter 5.

The balloon 5a of the balloon catheter 5 is connected to the contrast media passage port 5b through the contrast media passage lumen 5e. Thus, the contrast media may be injected into or extracted from the contrast media passage lumen 5e by manipulating a balloon inflation syringe 5c so as to inflate or deflate the balloon 5a.

Moreover, the guidewire 6 is inserted into the guidewire passage lumen 5f. The guidewire passage lumen 5f formed inside the balloon catheter 5 extends from the distal end of the balloon catheter 5 to reach the guidewire passage opening 5b. It should be noted that the distal end of the guidewire passage lumen 5f is adjacent to the balloon 5a, and the proximal end of the guidewire passage lumen 5f forms the guidewire passage opening 5b.

The guidewire 6 passes through the guidewire passage lumen 5f so that the distal portion of the guidewire 6 closely passes by the balloon 5a, and the proximal portion of the guidewire 6 passes through the guidewire passage opening 5b to exit from the balloon catheter 5.

As stated, the balloon catheter 5 of a dual lumen structure having the guidewire passage lumen 5f extending through the contrast media passage lumen 5e over almost the entire length of the balloon catheter 5 is called an "over-the-wire type balloon catheter". On the contrary, a balloon catheter called a "monorail type balloon catheter" has an alternative structure in which a guidewire passage lumen is formed only in the vicinity of the distal portion of the balloon catheter and the guidewire exits from the middle of the balloon catheter.

Procedures of PCI treatment will be explained hereinafter with reference to the over-the-wire type balloon catheter. FIG. 1A is an illustration of conventional PCI treatment, and FIGS. 2A through 2D are sequential illustrations of PCI treatment.

(1) First, a portion of the femoral artery or the brachial artery of a patient is punctured with a needle to make an opening so that the introducer set 3 can be installed at the opening of the artery.

Then, the guiding catheter 4 is pushed through the introducer set 3 so as to reach a place near an inlet of the coronary artery (FIG. 1A).

(2) The Y-connector 2 is coupled with the guiding catheter 4. Subsequently, the guidewire 6 may be introduced into the Y-connector 2 so as to pass through the guiding catheter 4, thereby placing the distal end of the guidewire 6 in the coronary artery (FIGS. 1A and 1B).

(3) Next, the proximal end of the guidewire 6 is inserted into the guidewire passage lumen 5f adjacent to the balloon 5a of the balloon catheter 5. By thrusting the guidewire 6 forward, the proximal end of the guidewire 6 travels through the guidewire passage lumen 5f and exits from the guidewire passage opening 5b. The balloon catheter 5 is introduced into the artery by using the guidewire 6 as something like a railroad, so that the balloon catheter 5 can be easily slid through the artery.

(4) When the balloon 5a of the balloon catheter 5 arrives at the coronary artery, the contrast media is injected into the coronary artery by way of the manifold 9. With the help of the contrast media, the physician can identify the position of a stenotic lesion D (i.e. a narrow portion of the coronary artery) on an X-ray fluoroscope.

Figure 2A:
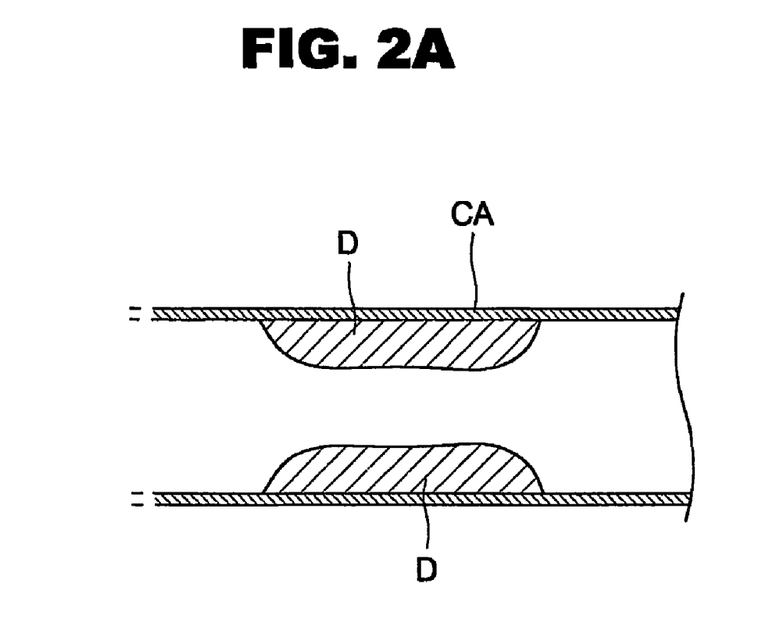
FIGS. 2A through 2D are the sequential illustrations of PCI treatment for the stenotic lesion D occurring in the coronary artery CA of the patient P, using the balloon catheter 5 and the stent 8.
Figure 2B:
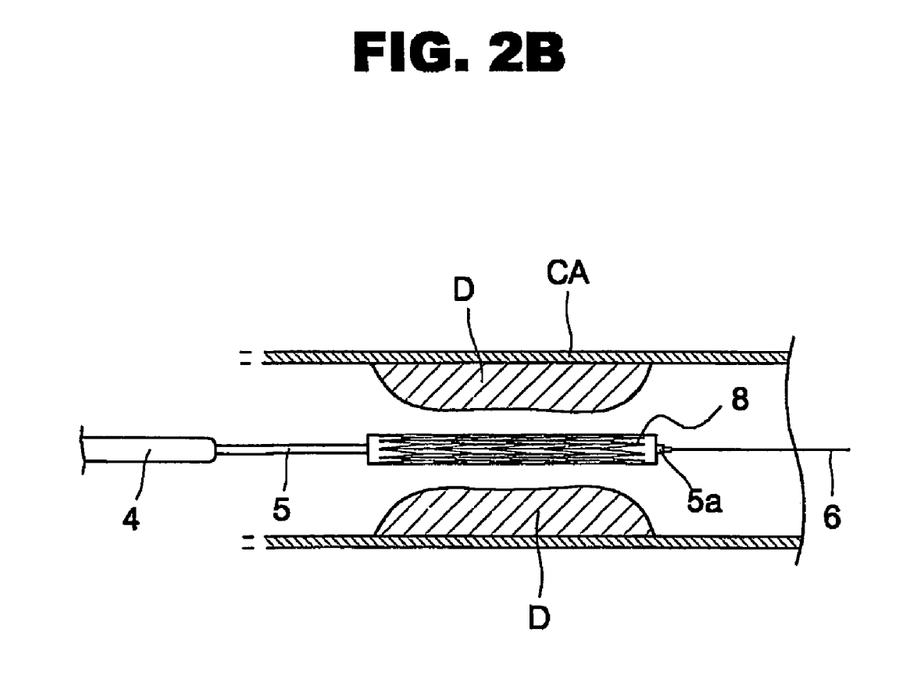
Figure 2C:
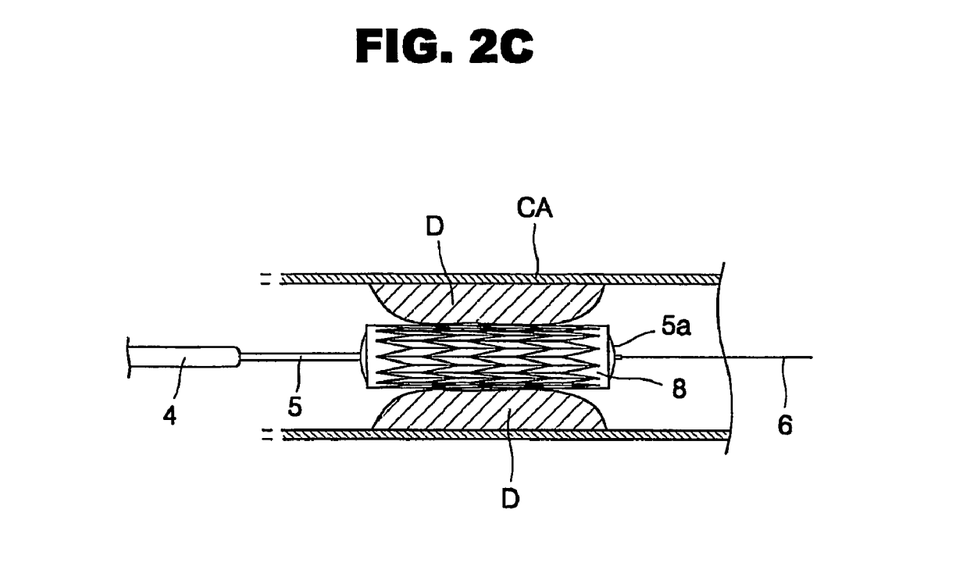
Figure 2D:
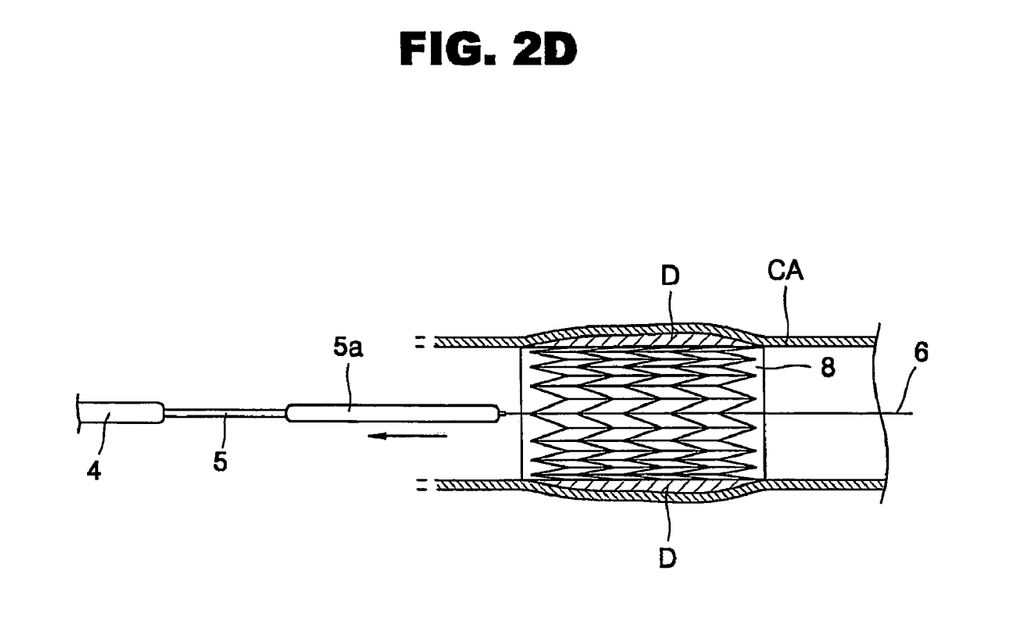

(5) By moving the balloon catheter backward or forward in the artery, the physician can place the balloon 5a mounted at the distal end of the balloon catheter 5 and the stent 8 mounted on the balloon 5a in the exact position of the stenotic lesion D (FIGS. 2A and 2B). When the contrast media contained in the balloon inflation syringe 5c is injected into the balloon 5a by way of the contrast media passage lumen 5e of the balloon catheter 5, the balloon 5a inflates so as to expand the stent 8 radially outward (FIG. 2C). The expanded stent holds up the artery walls that have been occluded due to the stenotic lesion D, so as to prevent recontraction of the walls. After the stent 8 is completely secured to the artery walls, the balloon 5a may be deflated by manipulating the balloon inflation syringe 5c conversely. Then, the balloon catheter 5 may be pulled out of the guiding catheter 4 to leave the stent 8 behind in the coronary artery (FIG. 2D).

The conventional PCI treatment stated above requires that the physician must move the balloon catheter 5 very minutely on the guidewire 6, relying on the sense of his or her hands while watching the X-ray fluoroscope, in order to place the balloon 5a in the exact position of the stenotic lesion D. However, it is very difficult for even a physician having great manual skills at pushing forward or pulling backward the balloon catheter in the artery, to adjust the balloon exactly to the position of the stenotic lesion in a short time. Thus, a key to the success of PCI treatment is that the stent should be installed exactly at the position of the stenotic lesion.

To position the balloon and stent exactly in the middle of the stenotic lesion of a coronary artery in PCI treatment, the physician has to inject the radioactive contrast dye multiple times into the coronary artery while moving the balloon catheter manually. The accurate positioning of the balloon and stent depends on the physician's hands and is not an easy task. The balloon and stent usually tend to move more or less than desired. However, even if the physician pays much attention to his or her manual movements, it is usually difficult to attain perfect positioning of the balloon and stent on a stenotic lesion of the coronary artery.

In PCI treatment using the conventional catheter apparatus, since the physician has to make small changes to the position of the balloon catheter by depending on his or her manual dexterity, it is very difficult to install the stent exactly at the position of the stenotic lesion (especially, at a curved or tortuous lesion) due to an excessive movement of the balloon and stent in the arteries. This may result in the installation of the stent in a less than optimal position, thereby causing less than ideal results. In addition, it takes much time to perform PCI treatment using the conventional catheter apparatus. Accordingly, the patient has to experience much pain due to the extended time of the operation, thereby adversely affecting the patient's prognosis.

SUMMARY OF THE INVENTION

The present invention provides an improved catheter apparatus for PCI capable of accurately positioning the balloon and stent at the site of an obstructive coronary artery lesion in such a convenient way that the accuracy of the PCI treatment can be enhanced and the operation time can be reduced.

To accomplish the above object, a catheter apparatus for PCI according to the present invention includes an introducer set 130 introduced to an opening of the human artery; a guiding catheter 140 introduced through the introducer set 130 and into the artery so as to extend a predetermined distance into the artery; a Y-connector 110 having a main tube 111 and a side tube 112 which branches off from the main tube 111, the Y-connector being coupled with the guiding catheter 140; a guidewire 160 introduced into the main tube 111 and the guiding catheter 140; a balloon catheter 150 introduced into the guiding catheter 140, having a balloon at the distal end thereof and a passage formed longitudinally through the balloon catheter 150, the passage providing a route for the guidewire 160; a minute adjustment portion 190 including a nut 192 and a minute adjustment bolt 191 engaging with the screw thread formed on the inner walls of the nut 192 and rotating so as to move backward or forward through the nut 192, the minute adjustment bolt 191 having a through hole 191b formed longitudinally thereinside so that the balloon catheter 150 can pass through the through hole 191b; a combining frame 120 having two legs, one leg being coupled with the circumferential surface of the main tube 111 and the other leg being coupled with the circumferential surface of the nut 192; and a clamping portion for holding the balloon catheter 150 passing through the minute adjustment portion 190 firmly in position.

Also, an alternative catheter apparatus for PCI according to the present invention to accomplish the above object, comprises an introducer set 130 introduced to an opening of the human artery; a guiding catheter 140 introduced through the introducer set 130 and into the artery so as to extend a predetermined distance into the artery; a Y-connector 110 having a main tube 111 and a side tube 112 which branches off from the main tube 111, the Y-connector being coupled with the guiding catheter 140; a guidewire 160 introduced into the main tube 111 and the guiding catheter 140; a balloon catheter 150 introduced into the guiding catheter 140, having a balloon at the distal end thereof and a passage formed longitudinally through the balloon catheter 150, the passage providing a route for the guidewire 160; a first bolt 195 coupled with the main tube 111 and having a screw portion on its circumferential surface, the screw portion wound in a predetermined direction; a second bolt 196 having a screw portion on its circumferential surface, the screw portion wound in an opposite direction to the screw portion of the first bolt 195, the end portion of the second bolt 196 being coupled with the end portion of the first bolt 195; a minute adjustment nut 193 having two oppositely wound screw portions and being coupled with the first and second bolts 195 and 196, concurrently, one screw portion engaging with the first bolt 195 and wound in the same way as the screw thread of the first bolt 195, and the other screw portion engaging with the second bolt 196 and wound in the same way as the screw thread of the second bolt 196; and a clamping portion for holding the balloon catheter 150 passing through the minute adjustment nut 193 firmly in position.

BRIEF DESCRIPTION OF THE DRAWINGS

The above and other features and advantages of the present invention will become more apparent by describing in detail exemplary embodiments thereof with reference to the attached drawings in which.

BEST MODE FOR CARRYING OUT THE INVENTION

Hereinafter, the catheter apparatus for PCI capable of accurately positioning stent and balloon in a desired position according to the present invention will be described with reference to the attached drawings.

Figure 3:
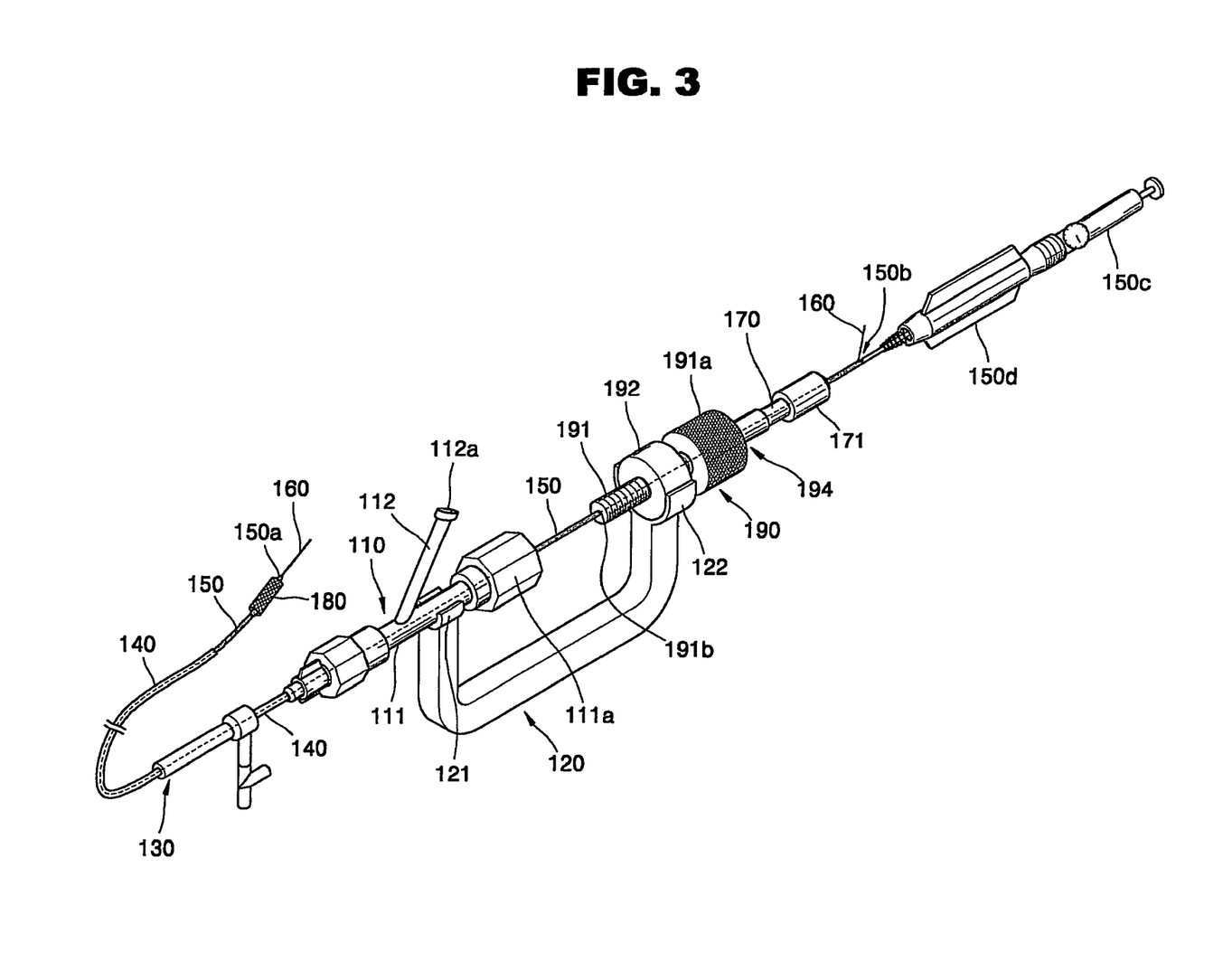
FIG. 3 shows a catheter apparatus for PCI capable of accurately positioning stent and balloon in a desired position according to a first embodiment of the present invention.
Figure 4:
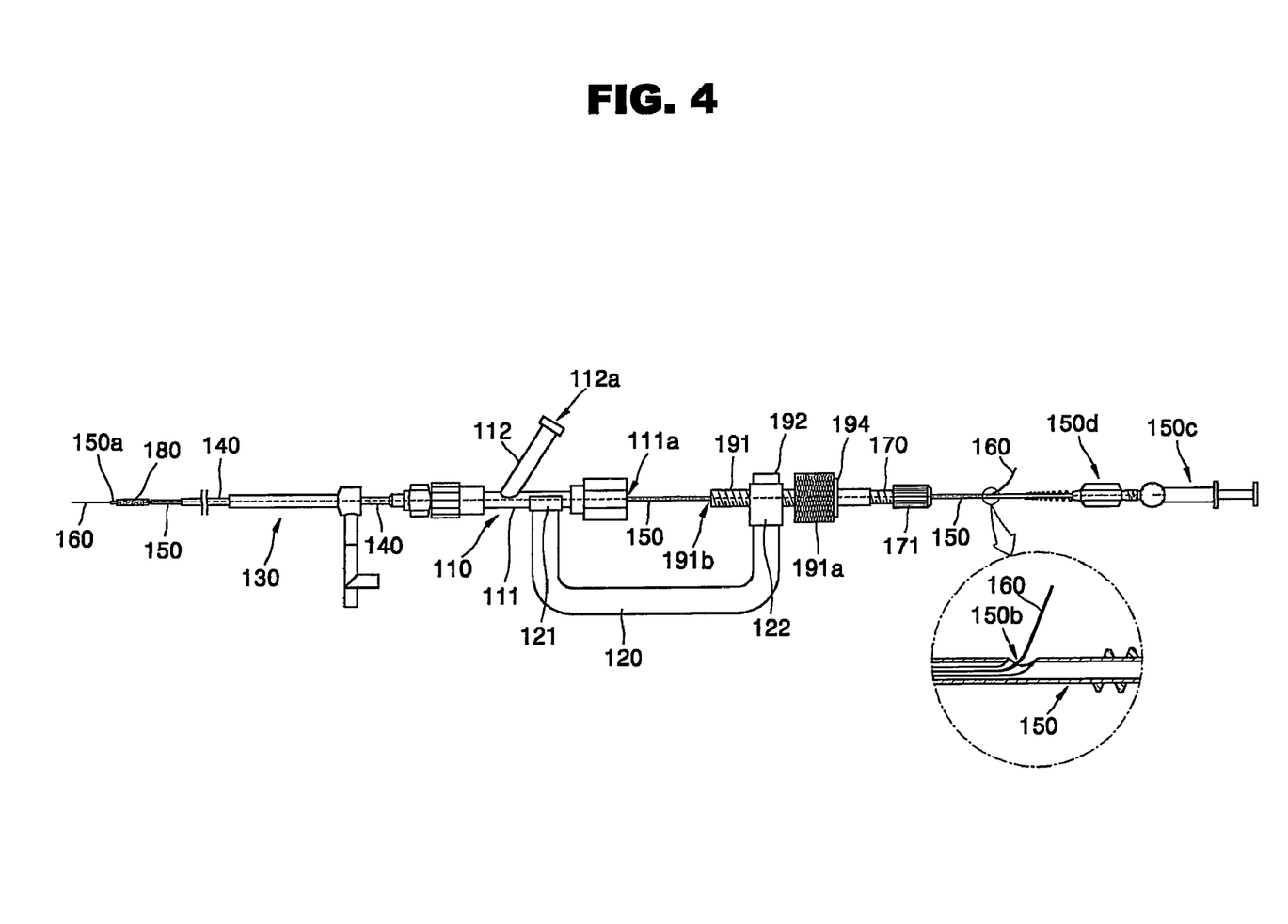
FIG. 4 is a side view of the catheter apparatus of FIG. 3.

FIG. 3 shows a catheter apparatus for PCI according to a first embodiment of the present invention. FIG. 4 is a side view of the catheter apparatus of FIG. 3, and FIG. 5 is a longitudinal cross-sectional view of the catheter apparatus of FIG. 3.

Figure 5:
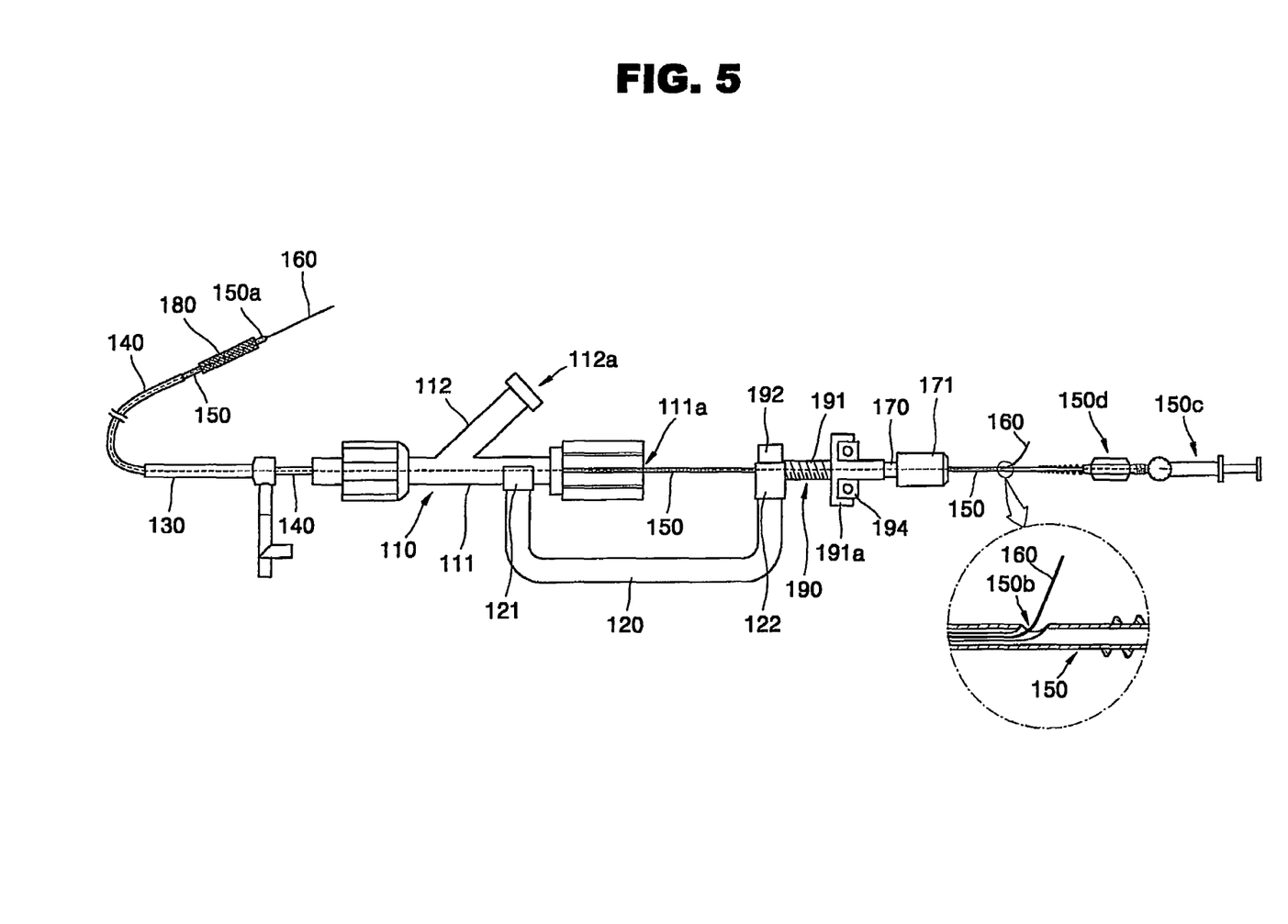
FIG. 5 is a longitudinal cross-sectional view of the catheter apparatus of FIG. 3.

Referring to FIGS. 3, 4 and 5, a Y-connector 110, an introducer set 130, a guiding catheter 140, a balloon catheter 150, a guidewire 160 and a stent 180 are the same as those shown in FIGS. 1B and 1C. Therefore, a detailed description of those components will be omitted.

The catheter apparatus 100 for PCI according to the present invention includes a U-shaped combining frame 120 with clips 121 and 122 formed at the respective ends thereof. The first clip 121 can be coupled with a circumferential surface of a main tube 111, and can be separated from the main tube 111 by pulling the first clip 121 from the circumferential surface of the main tube 111. Moreover, the second clip 122 formed at the other end of the combining frame 120 can be coupled with a circumferential surface of a nut 192, and can be separated from the nut 192 by pulling the second clip 122 from the circumferential surface of the nut 192.

A minute adjustment bolt 191 can be screwed back and forth through the nut 192. A minute adjustment portion 190 comprises the minute adjustment bolt 191, the nut 192, and a bearing 194 which is installed inside a rotating cylinder 191a. The rotating cylinder 191a is integrally formed as part of the minute adjustment bolt 191.

Rotation of the rotating cylinder 191a causes the minute adjustment bolt 191 to be screwed backward or forward through the nut 192.

The balloon catheter 150 passes through a through hole 191b of the minute adjustment bolt 191 and the main tube 111 of the Y-connector 110. Since the bearing 194 is installed inside the rotating cylinder 191a, the balloon catheter 150 maintain its straightness without getting twisted when the rotating cylinder 191a rotates. An inner wheel of the bearing 194 is integrated with a clamping bolt 170 which has a plurality of forks 170a. The outer surface of the forks 170a is formed with threads so that the forks 170a can be tightened up by a clamping nut 171.

The balloon catheter 150 passes through a through hole formed inside the clamping bolt 170 and extends in the direction of the longitudinal axis of the clamping bolt 170, and it further passes through a hole formed in the center of the clamping nut 171, so that the balloon catheter 150 can be fixed in place by tightening up the clamping nut 171.

As described above, the minute adjustment bolt 191, the bearing 194, the rotating cylinder 191a, the clamping bolt 170 and the clamping nut 171 are combined to form a minute adjustment portion for adjusting the position of the balloon catheter in an artery. Rotation of the rotating cylinder 191a causes the bearing 194, but not the clamping bolt 170 and clamping nut 171, to rotate. When the rotating cylinder 191a is rotated, the clamping bolt 170 and the clamping nut 171 do not rotate but move together with the minute adjustment bolt 191.

As shown, the balloon catheter 150 is prevented from moving with respect to the minute adjustment bolt 191 by means of the coupling of the clamping bolt 170 and the clamping nut 171, while not being twisted. Therefore, rotation of the rotating cylinder 191a in a clockwise or counterclockwise direction makes it possible to minutely move the balloon catheter 150 inward or outward with reference to the artery.

Since conventional catheter apparatuses for PCI are directly moved inward or outward through the artery by the physician's manual action, it is difficult for the physician to supply sufficiently small changes to the balloon catheter to exactly position the balloon catheter.

However, since the catheter apparatus 100 for PCI according to the present invention as stated above permits the balloon catheter 150 to move as little as just one thread pitch along the screw thread formed on the circumferential surface of the minute adjustment bolt 191 per one rotation of the minute adjustment bolt 191, the physician can more accurately and reliably manipulate the movement of the balloon catheter in an artery.

Reference numeral 150b denotes a guidewire passage opening through which the guidewire 160 passes so as to exit from the balloon catheter, and reference numeral 150c denotes a balloon inflation syringe containing the contrast media which can be injected into the balloon inflation port 150d, and reference numeral 151 denotes the contrast media passage lumen that is connected to the balloon. After placing the balloon 150a in the desired position of the coronary artery, the physician presses the balloon expansion syringe 150c so that the contrast media passes through the contrast media passage lumen 151 to inflate the balloon 150a. Inflation of the balloon 150a causes the stent 180 to expand radially outward so that the stent dilates the occluded, narrow portion of the coronary artery to enable the blood to flow more freely.

Reference numeral 150d denotes a balloon inflation port through which the contrast media passes so as to inflate the balloon.

The guidewire 160 is introduced into a guidewire passage lumen 152 partly adjoining the balloon 150a at the distal end of the balloon catheter 150, and exits from the balloon catheter 150 at a predetermined position along the balloon catheter 150 through the guidewire passage opening 150b. Moreover, reference numeral 112a denotes a manifold connection port with which the manifold 9 may be coupled as shown in FIGS. 1B and 1C.

Figure 6:
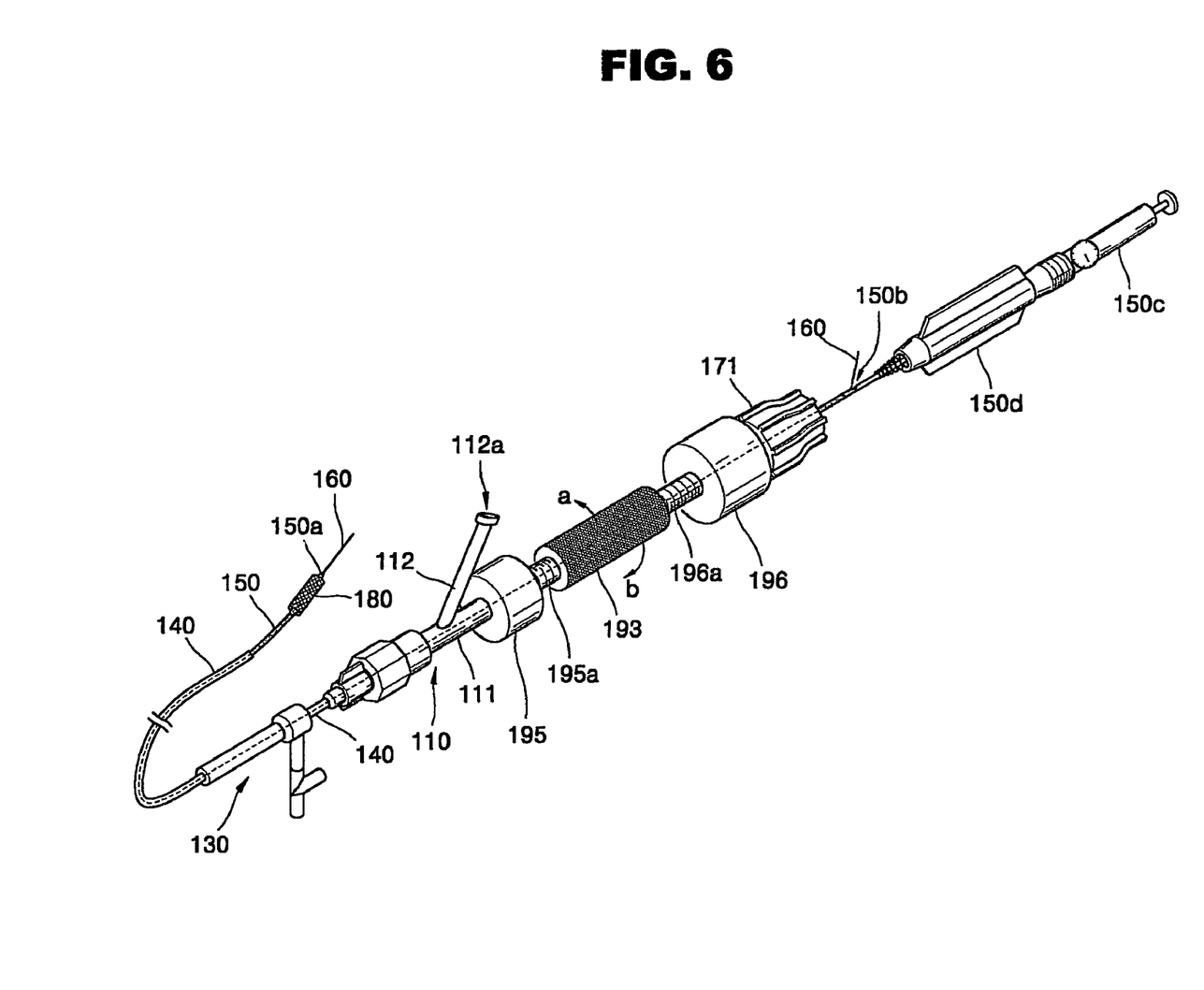
FIG. 6 shows a catheter apparatus for PCI capable of accurately positioning stent and balloon in a desired position according to a second embodiment of the present invention.
Figure 7:
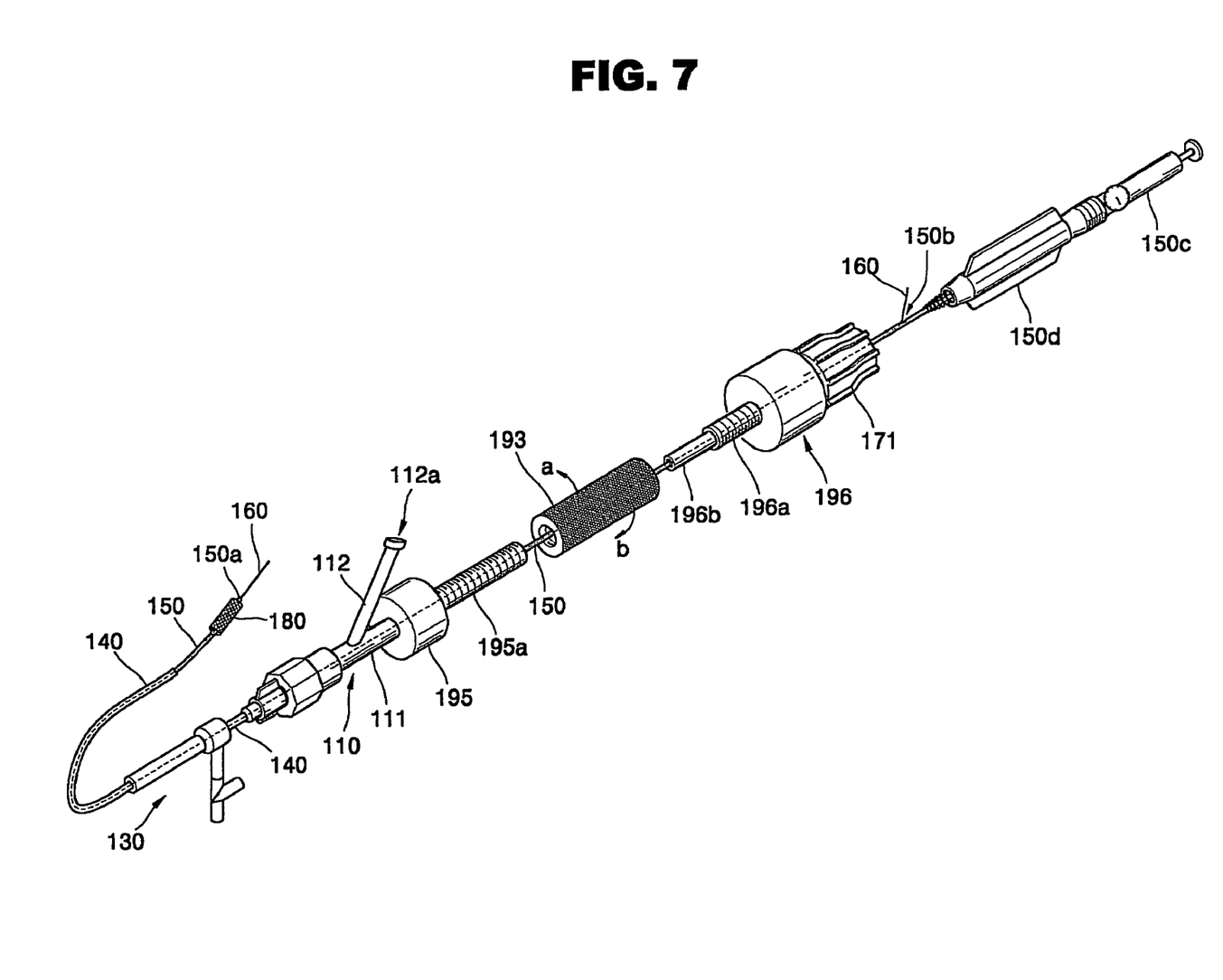
FIG. 7 is an illustration of the catheter apparatus of FIG. 6, with the parts of the balloon catheter disassembled.
Figure 8:
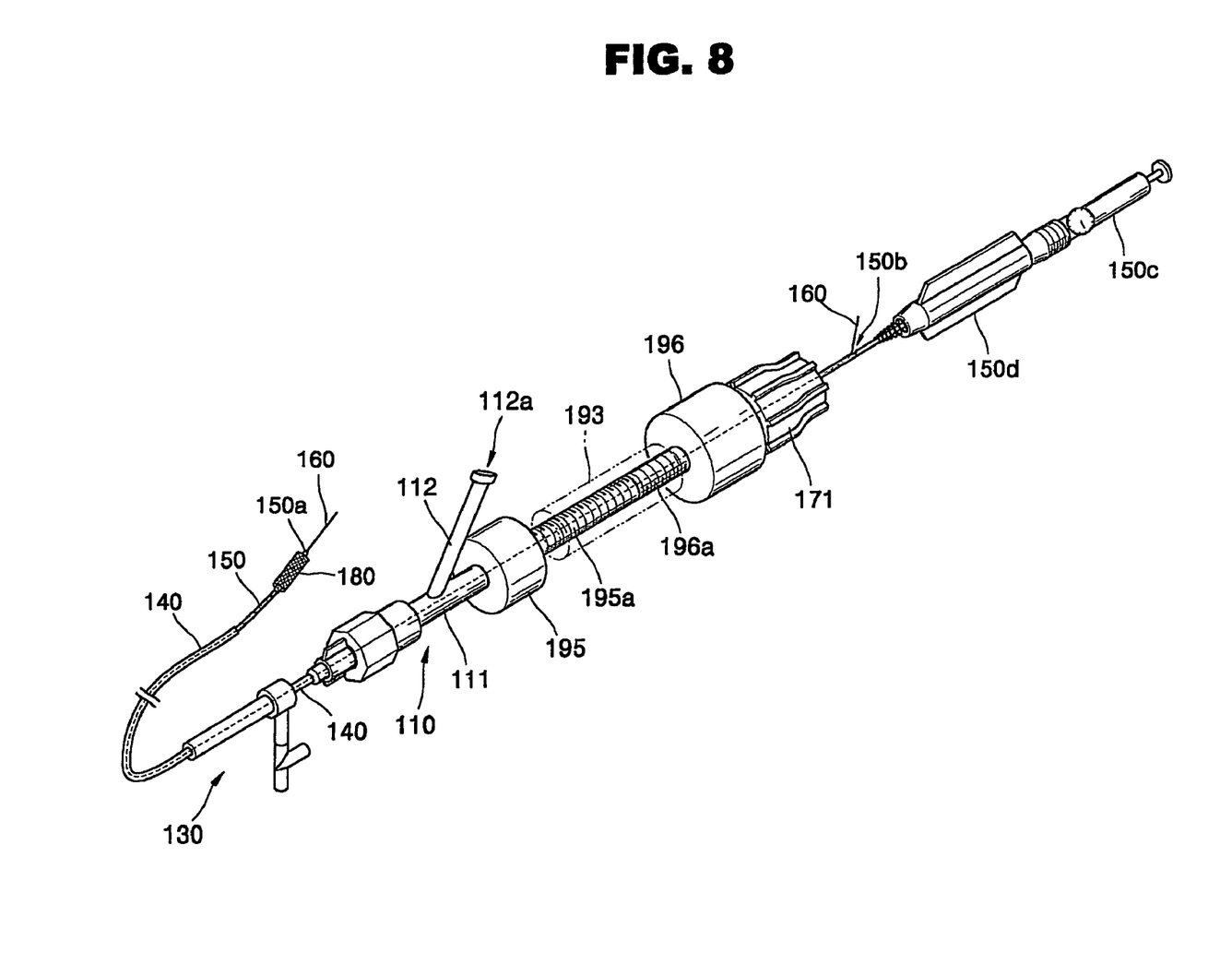
FIG. 8 is a perspective view of the catheter apparatus of FIG. 7, excluding the minute adjustment nut 193 therefrom.
Figure 9A:
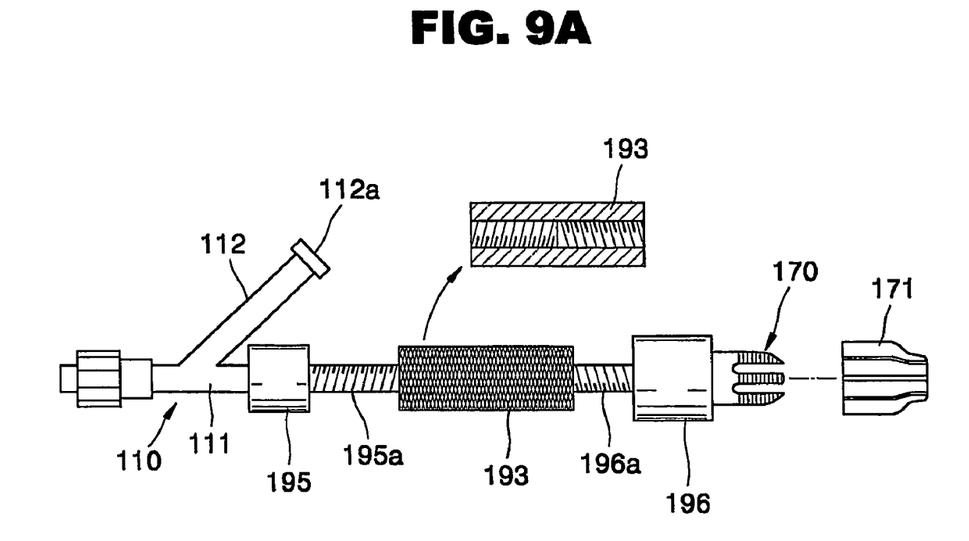
FIG. 9A is a detailed view of the Y-connector 110 and the minute adjustment nut 193 of the apparatus shown in FIG. 6.
Figure 9B:
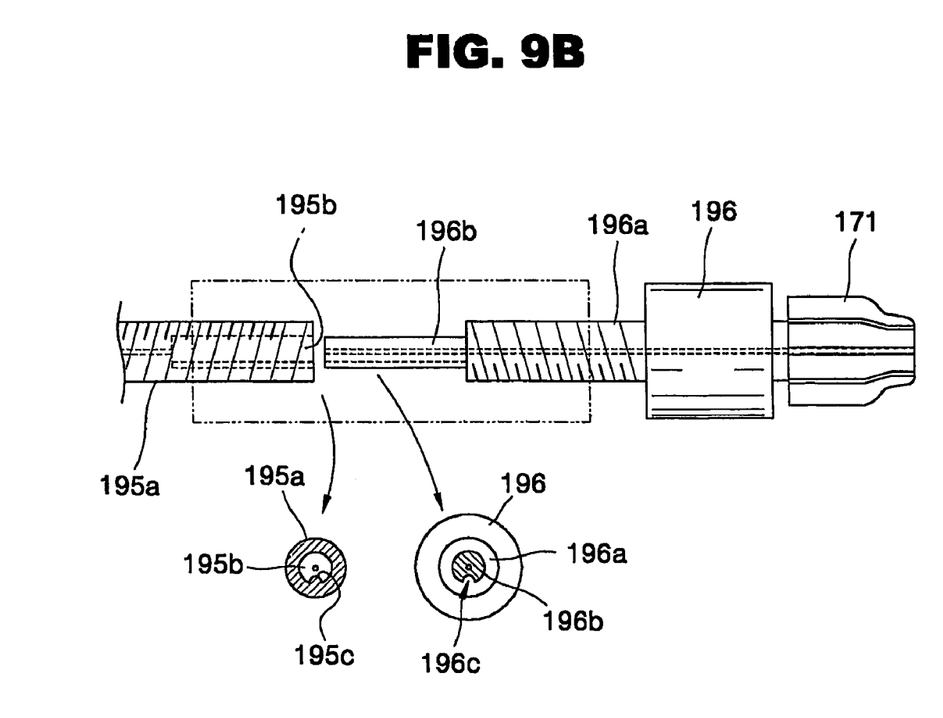
FIG. 9B shows the combination of a first bolt 195 and a second bolt 196.

FIG. 6 shows a catheter apparatus for PCI according to a second embodiment of the present invention. FIG. 7 is an illustration of the catheter apparatus of FIG. 6, with certain parts of the apparatus disassembled, and FIG. 8 is a perspective view of the catheter apparatus of FIG. 7, excluding the minute adjustment nut 193. FIG. 9A is a detailed view of the Y-connector 110 and the minute adjustment nut 193 of the apparatus shown in FIG. 6, and FIG. 9B shows the combination of a first bolt 195 and a second bolt 196.

The catheter apparatus for PCI according to the second embodiment of the present invention differs from that of the first embodiment stated above, in that the mechanism for minutely adjusting the insertion position of the balloon catheter in the artery comprises a first bolt 195, a second bolt 196 and a minute adjustment nut 193.

The first bolt 195 is integrated with the main tube 111 of the Y-connector 110, and it has a first screw portion 195a on its circumferential surface. The second bolt 196 has a second screw portion 196a on its circumferential surface. The screw thread of the first screw portion 195a is wound in the opposite direction to the screw thread of the second screw portion 196a. That is, assuming the first screw portion 195a has a left hand screw thread on its circumferential surface, the second screw portion 196a has a right hand screw thread on its circumferential surface, or vice versa.

Referring to FIG. 9A, two screw portions are formed on the inner walls of the through hole of the minute adjustment nut 193; the two screw portions correspond with the first and second screw portions 195a and 196a, respectively, and one screw portion has its screw thread wound in the opposite direction to the screw thread of the other screw portion. That is, the screw portion formed inside the minute adjustment nut 193 and engaging with the first bolt 195 is wound in the same direction as the first screw portion 195a, and the screw portion formed inside the minute adjustment nut 193 and engaging with the second bolt 196 is wound in the same direction as the second screw portion 196a.

Referring to FIG. 9B, the first bolt 195 has a receiving hole 195b which extends along the central axis of the first bolt 195. The second bolt 196 has a core 196b extending from the end surface of the second screw portion 196a. The core 196b is inserted into the receiving hole 195b.

The receiving hole 195b has a protruding key 195c on the inner walls thereof, and the core 196b has a key groove 196c formed on the surface thereof. Thus, the protruding key 195c of the receiving hole 195b engages with the key groove 196c of the core 196b. Meanwhile, the clamping bolt 170 is integrated with the second bolt 196.

In accordance with the above described configuration, the first and second bolts 195 and 196 remained untwisted without rotating with respect to each other during the rotation of the minute adjustment nut 193, so that they move towards or apart from each other when the minute adjustment nut 193 rotates in the direction of "A" or "B" as shown in FIGS. 6 and 7. That is, assuming that the first screw portion 195a formed on circumferential surface of the first bolt 195 is a left hand screw and the second screw portion 196a formed on the circumferential surface of the second bolt 196 is a right hand screw, rotation of the minute adjustment nut 193 in the direction of "A" causes the first and second bolts 195 and 196 to move apart from each other so that the balloon catheter 150 moves outward from the artery. On the contrary, rotation of the minute adjustment nut 193 in the direction of "B" causes the first and second bolts 195 and 196 to move towards each other so that the balloon catheter 150 moves toward the inside of the artery.

As for the catheter apparatus for PCI according to the second embodiment of the present invention, one rotation of the minute adjustment nut 193 causes the balloon catheter 150 to move back or forth into an artery by two thread pitches of the screw thread of the minute adjustment nut 193. Thus, the physician can adjust the insertion position of the balloon catheter 150 with greater accuracy by rotating the minute adjustment nut 193 little by little so that the balloon 150a secured to the distal end of the balloon catheter 150 can be placed in the exact position where the stenotic lesion occurs.

As for the catheter apparatus for PCI according to the second embodiment of the present invention, the first bolt 195 has the receiving hole 195b thereinside, and the second bolt 196 has a core 196b. Moreover, the receiving hole 195b has the protruding key 195c on its inner walls, and the core 196b has the key groove 196c on its circumferential surface.

However, it is also possible to make variations in the configuration of the of the first and second bolts 195 and 196 as stated above so that the first and second bolts do not rotate with respect to each other in spite of the rotation of the minute adjustment nut 193.

According to the catheter apparatus for PCI provided by the present invention, the physician can minutely and conveniently adjust the insertion position of the balloon catheter by rotating a control handle (i.e. the rotating cylinder or minute adjustment nut) little by little while watching the X-ray fluoroscope so that PCI treatment requiring high precision and accuracy in placing the balloon and stent in the exact position of stenotic lesion can be performed successfully, performed successfully, thereby reducing the operation time.

Furthermore, the mechanical configuration according to the present invention making it possible to minutely adjust the insertion position of the balloon catheter can be easily adapted to any other catheter apparatus for introducing a catheter into the human internal organs such as the peripheral arteries, the urethra, the bronchi, the gall tubes, etc., for medical analysis and/or treatment, thereby allowing the position of the distal end of the catheter to be conveniently and minutely adjusted.

While the present invention has been particularly shown and described with reference to exemplary embodiments thereof, it will be understood by those of ordinary skill in the art that various changes in form and details may be made therein without departing from the spirit and scope of the present invention as defined by the following claims.

The invention claimed is:

1. A catheter apparatus for percutaneous coronary intervention capable of accurately positioning stent and balloon in a desired position, comprising:
   an introducer set 130 introduced to an opening of the human artery;
   a guiding catheter 140 introduced through the introducer set 130 and into the artery so as to extend a predetermined distance into the artery;
   a Y-connector 110 having a main tube 111 and a side tube 112 which branches off from the main tube 111, the Y-connector being coupled with the guiding catheter 130;
   a guidewire 160 introduced into the main tube 111 and the guiding catheter 140;
   a balloon catheter 150 introduced into the guiding catheter 140, having a balloon at the distal end thereof and a passage formed longitudinally through the balloon catheter, the passage providing a route for the guidewire 160;
   a minute adjustment portion 190 including a nut 192 and a bolt 191 engaging with a screw thread formed on the inner walls of the nut 192 and rotating so as to move backward or forward through the nut 192, the bolt 191 having a through hole 191*b* formed longitudinally thereinside so that the balloon catheter 150 passes through the through hole 191*b*;
   a combining frame 120 having two legs, one leg being coupled with the circumferential surface of the main tube 111 and the other leg being coupled with the circumferential surface of the nut 192; and
   a clamping portion for holding the balloon catheter 150 passing through the minute adjustment portion 190 firmly in position.

2. The catheter apparatus as claimed in claim 1, wherein the combining frame 120 includes a first clip 121 coupled with the circumferential surface of the main tube 111 and capable of being separated from the main tube 111, and a second clip 122 coupled with the circumferential surface of the nut 192 and capable of being separated from the nut 192.

3. The catheter apparatus as claimed in claim 1, wherein the minute adjustment portion 190 further comprises a rotating cylinder 191*a* integrally formed with the bolt 191.

4. The catheter apparatus as claimed in claim 1, wherein the clamping portion includes a bearing 194 formed inside the bolt 191, a clamping bolt 170 fixed to the bearing 194, and a clamping nut 171 cooperating with the clamping bolt 170 to hold the balloon catheter 150 passing through the bearing 194 firmly in position.

5. The catheter apparatus as claimed in claim 3, wherein the clamping portion includes a bearing 194 formed inside the bolt 191, a clamping bolt 170 fixed to the bearing 194, and a clamping nut 171 cooperating with the clamping bolt 170 to hold the balloon catheter 150 passing through the bearing 194 firmly in position.

6. A catheter apparatus for percutaneous coronary intervention capable of accurately positioning stent and balloon in a desired position, comprising:
   an introducer set 130 introduced to an opening of the human artery;
   a guiding catheter 140 introduced through the introducer set 130 and into the artery so as to extend a predetermined distance into the artery;
   a Y-connector 110 having a main tube 111 and a side tube 112 which branches off from the main tube 111, the Y-connector being coupled with the guiding catheter 130;
   a guidewire 160 introduced into the main tube 111 and the guiding catheter 140;
   a balloon catheter 150 introduced into the guiding catheter 140, having a balloon at the distal end thereof and a passage formed longitudinally through the balloon catheter, the passage providing a route for the guidewire 160;
   a first bolt 195 fixedly coupled with the main tube 111 and having a screw portion on its circumferential surface, the screw portion wound in a predetermined direction;
   a second bolt 196 having a screw portion on its circumferential surface, the screw portion of the second bolt wound in an opposite direction to the screw portion of the first bolt 195, an end portion of the second bolt 196 being coupled with an end portion of the first bolt 195;
   a minute adjustment nut 193 having two oppositely wound screw portions and being concurrently coupled with the first and second bolts 195 and 196, one screw portion engaging with the first bolt 195 and wound in the same way as the screw thread of the first bolt 195, and the other screw portion engaging with the second bolt 196 and wound in the same way as the screw thread of the second bolt 196; and
   a clamping portion for holding the balloon catheter 150 passing through the minute adjustment nut 193 firmly in position.

7. The catheter apparatus as claimed in claim 6, wherein the clamping portion includes a clamping bolt 170 fixed to the second bolt 196 and a clamping nut 171 cooperating with the clamping bolt 170 to hold the balloon catheter 150 firmly in position.

8. The catheter apparatus as claimed in claim 6, wherein the first bolt 195 has a receiving hole 195*b* extending along the central axis of the first bolt 195 from the threaded end of the first bolt 195 a predetermined distance thereinto and having a protruding key 195*c* on the inner walls thereof, and the second bolt 196 has a core 196*b* exending from the end surface of the screw portion of the second bolt 196 and inserted into the receiving hole 195*b*, the core 196*b* having a key groove 196*c* formed on the surface thereof to couple with the protruding key 195*c*.

9. The catheter apparatus as claimed in claim 6, wherein the first bolt 195 has a receiving hole 195*b* extending along the central axis of the first bolt 195 from the threaded end of the first bolt 195 a predetermined distance thereinto and having a key groove formed on the inner walls thereof, and the second bolt 196 has a core 196*b* exending from the end surface of the screw portion of the second bolt 196 and inserted into the receiving hole 195*b*, the core 196*b* having a protruding key formed on the circumferential surface thereof to couple with the key groove.

10. The catheter apparatus as claimed in claim 6, wherein the first bolt 195 has a core exending along the central axis of the first bolt 195 and having a protruding key on the circumferential surface thereof, and the second bolt 196 has a receiving hole having a key groove formed on the inner walls thereof, the key groove being couple with the protruding key.

11. The catheter apparatus as claimed in claim 6, wherein the first bolt 195 has a core exending along the central axis of the first bolt 195 and having a key groove formed on the circumferential surface thereof, and the second bolt 196 has a receiving hole having a protruding key on the inner walls thereof, and receiving the core, the protruding key being couple with the key groove.

* * * * *